United States Patent
Saeki

(10) Patent No.: US 10,463,342 B2
(45) Date of Patent: Nov. 5, 2019

(54) ULTRASONIC TRANSDUCER

(71) Applicant: NIHON DEMPA KOGYO CO., LTD., Tokyo (JP)

(72) Inventor: Isao Saeki, Saitama (JP)

(73) Assignee: NIHON DEMPA KOGYO CO., LTD., Tokyo (JP)

( * ) Notice: Subject to any disclaimer, the term of this patent is extended or adjusted under 35 U.S.C. 154(b) by 226 days.

(21) Appl. No.: 15/311,191

(22) PCT Filed: May 18, 2015

(86) PCT No.: PCT/JP2015/064177
§ 371 (c)(1),
(2) Date: Nov. 15, 2016

(87) PCT Pub. No.: WO2015/178341
PCT Pub. Date: Nov. 26, 2015

(65) Prior Publication Data
US 2017/0079614 A1 Mar. 23, 2017

(30) Foreign Application Priority Data
May 20, 2014 (JP) .................................. 2014-104293

(51) Int. Cl.
A61B 8/12 (2006.01)
F16D 3/68 (2006.01)
A61B 8/00 (2006.01)

(52) U.S. Cl.
CPC ............... *A61B 8/12* (2013.01); *A61B 8/445* (2013.01); *A61B 8/4461* (2013.01); *F16D 3/68* (2013.01)

(58) Field of Classification Search
None
See application file for complete search history.

(56) References Cited

U.S. PATENT DOCUMENTS

| 4,151,834 A * | 5/1979 | Sato ..................... A61B 8/08 367/104 |
| 5,050,446 A * | 9/1991 | Takashima ............ F16F 15/124 464/180 |
| 5,479,929 A * | 1/1996 | Cooper .................... A61B 8/12 600/459 |

FOREIGN PATENT DOCUMENTS

| CN | 1720006 | 1/2006 |
| CN | 102138809 | 8/2011 |
| CN | 103767736 | 5/2014 |
| JP | H07-30812 | 4/1995 |

(Continued)

OTHER PUBLICATIONS

"International Search Report (Form PCT/ISA/210) of PCT/JP2015/064177", dated Jul. 7, 2015, with English translation thereof, pp. 1-4.

(Continued)

*Primary Examiner* — Katherine L Fernandez
(74) *Attorney, Agent, or Firm* — JCIPRNET

(57) ABSTRACT

During normal and reverse swings of a transducer main body, an engagement accuracy is ensured to reduce generation of vibration and noise. An ultrasonic transducer includes: a coupling swingably and loosely fitted between one end portion of an output shaft of a power source that swings the transducer main body and the transducer main body, and a flywheel swingably and loosely fitted to another end portion of an output shaft of the power source, ensuring the reduced vibration and noise from the transducer main body.

5 Claims, 6 Drawing Sheets

(56) References Cited

FOREIGN PATENT DOCUMENTS

| | | |
|---|---|---|
| JP | H09-222826 | 8/1997 |
| JP | 2001-327501 | 11/2001 |
| JP | 2004033485 | 2/2004 |
| JP | 2004-316672 | 11/2004 |
| JP | 2011-12688 | 1/2011 |
| JP | 2015-027320 | 2/2015 |
| WO | 2008-093861 | 8/2008 |

OTHER PUBLICATIONS

"Office Action of China Counterpart Application," dated Dec. 21, 2018, with English translation thereof, p. 1-p. 14.

* cited by examiner

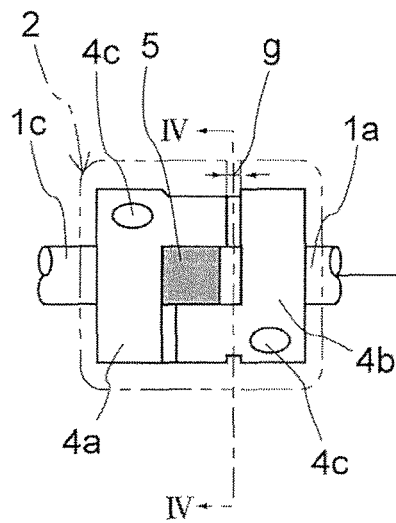
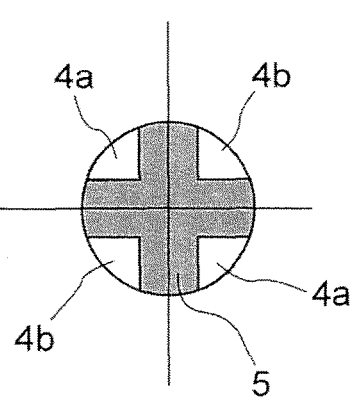
FIG. 4(a)   FIG. 4(b)
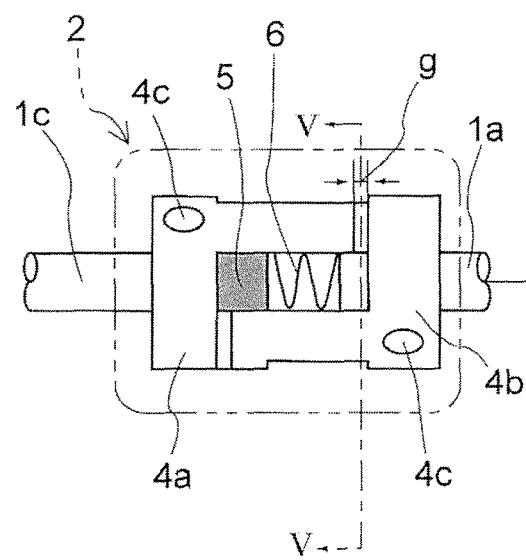
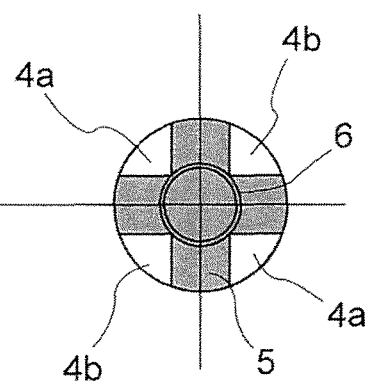
FIG. 5(a)   FIG. 5(b)

ULTRASONIC TRANSDUCER

CROSS-REFERENCE TO RELATED APPLICATION

This application is a 371 of international application of PCT application serial no. PCT/JP2015/064177, filed on May 18, 2015, which claims the priority benefits of Japan application no. 2014-104293, filed on May 20, 2014. The entirety of each of the abovementioned patent applications is hereby incorporated by reference herein and made a part of this specification.

TECHNICAL FIELD

The present invention relates to a mechanical scanning 3D ultrasonic transducer for medical ultrasonic diagnostic equipment, especially, relates to an ultrasonic transducer with a combination of a coupling and a flywheel. The coupling internally includes a buffer between a power source, which drives a transducer main body, and a transducer. This ensures the reduced vibration and noise from the transducer main body.

BACKGROUND ART

A conventional ultrasonic transducer, for example, a medical mechanical scanning 3D ultrasonic transducer 10 that is transvaginal and transrectal, as shown in FIG. 7, includes a stepper motor 1, which is a driving source of a transducer main body 13, disposed in a housing 11 having a tip with a tapered shape. The conventional ultrasonic transducer includes hubs 4a, 4b, and 4c disposed between an output shaft 1a of the stepper motor 1 and a drive shaft 1c. Then, the hub 4c is screwed to the output shaft 1a of the stepper motor 1 while the hub 4a is screwed to the drive shaft 1c. Metallic disks 2a are each interposed and secured between two of the hubs 4a, 4b, and 4c to transmit torque of the output shaft 1a to the drive shaft 1c, causing the drive shaft 1c to swing by a predetermined angle in normal and reverse directions.

Then, the swing of this drive shaft 1c swings a large bevel gear 7b engaging a small bevel gear 7a on a tip of the drive shaft 1c. This causes normal and reverse swings of the ultrasound transmitting/receiving portion (a piezoelectric element group) 13 about its short-axis direction in ultrasonic propagation medium filled up in a cover 12 fitted into a tip of the housing 11.

When an ultrasonic diagnosis of a patient is performed using the mechanical scanning 3D ultrasonic transducer 10 for medical ultrasonic diagnostic equipment, a surface of the cover 12 of the ultrasonic transducer 10 is inserted into, for example, a vagina and/or a rectum of the patient for contacting their inner wall surfaces or is brought into contact with body surfaces to perform transmission and reception of an ultrasound after a cap 14 is fitted on a lower end portion of the housing 11 shown in FIG. 7 to causes the inside of the housing 11 to be in a sealed state.

Therefore, the mechanical scanning 3D ultrasonic transducer for medical ultrasonic diagnostic equipment, which has a structure that swings the transducer main body 13, is used while its distal end portion contacts the body surface or the inside of a body cavity, such as the vagina and the rectum, of the patient during the ultrasonic diagnosis. Thus, it is necessary that the patient does not feel a vibration, a noise, and/or the like from the transducer main body.

SUMMARY

Problems to be Solved

A conventional ultrasonic transducer of the ultrasonic diagnostic equipment having a structure, which swings the transducer main body 13, employs a stepper motor as a power source for swinging the transducer main body 13. Especially, as shown in FIG. 8, the hubs 4a, 4b, and 4c connect the output shaft 1a of the stepper motor 1 to the drive shaft 1c, which drives the small bevel gear 7a, with the disks 2a each interposed between the hubs 4a, 4b, and 4c. The conventional ultrasonic transducer employs a disk-type coupling 2 of a type where a torsional rigidity of the metallic disks 2a transmits the torque to the drive shaft 1c.

However, this type of conventional ultrasonic transducer of the ultrasonic diagnostic equipment, as described above, employs the stepper motor 1 as the driving source of the transducer main body 13 and employs the disk-type coupling 2 for the coupling. This causes a vibration in rotation direction of the stepper motor 1 to be directly transmitted to the transducer main body. This leads to uncomfortable vibration and noise for the patient.

Furthermore, the small bevel gear 7a and the large bevel gear 7b mesh to swing the transducer main body 13 (the piezoelectric element group) in the normal and reverse directions by a predetermined angle about its short-axis direction. Thus, both the gears have error between shafts of both the gears due to, for example, variation of assembly accuracy of both the bevel gears. This causes also individual difference of a backlash between the bevel gears. As a result, this causes a problem of individual difference in vibration level of the ultrasonic transducers as products.

Solutions to the Problems

An ultrasonic transducer of the present invention includes: a coupling swingably and loosely fitted between a transducer main body and a power source that swings the transducer main body, and a flywheel swingably and loosely fitted to an output shaft of the power source, to reduce a vibration and a noise from the transducer main body.

In the ultrasonic transducer of the present invention, the coupling is constituted of two hubs opposed to one another, and a buffer is disposed between the two hubs.

Furthermore, in the ultrasonic transducer of the present invention, a compression coil spring is disposed between the two hubs of the coupling in addition to the buffer.

In the ultrasonic transducer of the present invention, the coupling is disposed at one end portion of the output shaft, and the flywheel is disposed at the other end portion of the output shaft.

The buffer is made of silicon rubber.

Furthermore, the buffer has a cross shape in plan view.

Effects of the Invention

During normal and reverse swings of the transducer main body, an engagement accuracy is ensured to reduce generation of vibration and noise.

BRIEF DESCRIPTION OF THE DRAWINGS

FIG. 4(a) is an enlarged side view illustrating a coupling portion according to the embodiment of the ultrasonic transducer of the present invention shown in FIG. 2, and FIG. 4(b) is a front view viewed in IV-IV-arrow direction shown in FIG. 4(a).

FIG. 5(a) is an enlarged side view illustrating a coupling portion according to the embodiment of the ultrasonic transducer of the present invention shown in FIG. 3, and FIG. 5(b) is a front view viewed in V-V-arrow direction shown in FIG. 5(a).

DESCRIPTION OF PREFERRED EMBODIMENTS

Figure 1:
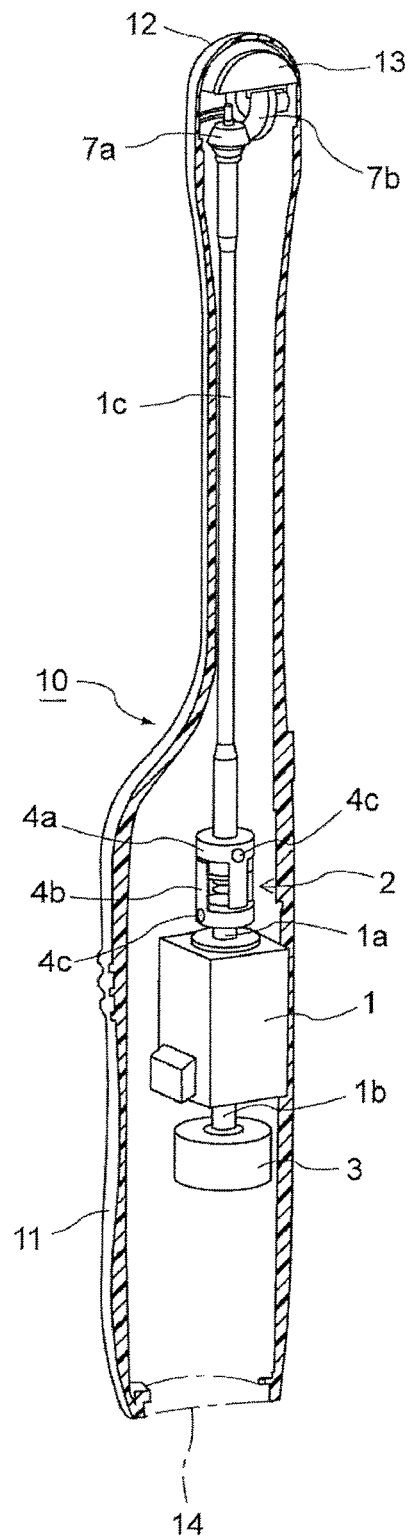
FIG. 1 is a longitudinal sectional drawing illustrating an overall configuration of a mechanical scanning 3D ultrasonic transducer for medical ultrasonic diagnostic equipment of the present invention.

The following description describes embodiments of the ultrasonic transducer of the present invention on the basis of the accompanying drawings.

Similarly to the above-described conventional mechanical scanning 3D ultrasonic transducer for medical ultrasonic diagnostic equipment, the ultrasonic transducer of the present invention includes a stepper motor 1, which is a power source of the transducer main body and is disposed in a housing 11 having a tapered-shaped tip. Between an output shaft 1a and a drive shaft 1c of the stepper motor 1, hubs 4a and 4b are disposed. Then, the hub 4b is screwed to the output shaft 1a of the stepper motor 1 while the hub 4a is screwed to the drive shaft 1c to engage both the hubs 4a and 4b. This causes torque of the output shaft 1a to be transmitted to the drive shaft 1c to swing the drive shaft 1c by a predetermined angle in normal and reverse directions. Then, the swing of the drive shaft 1c swings a large bevel gear 7b engaging a small bevel gear 7a fixedly secured to a tip of the drive shaft 1c. This causes an ultrasound transmitting/receiving portion (a piezoelectric element group) 13 to swing about its short-axis direction inside ultrasonic propagation medium of a cover 12 fitted into the tip of the housing 11 (see FIG. 1).

Figure 7:
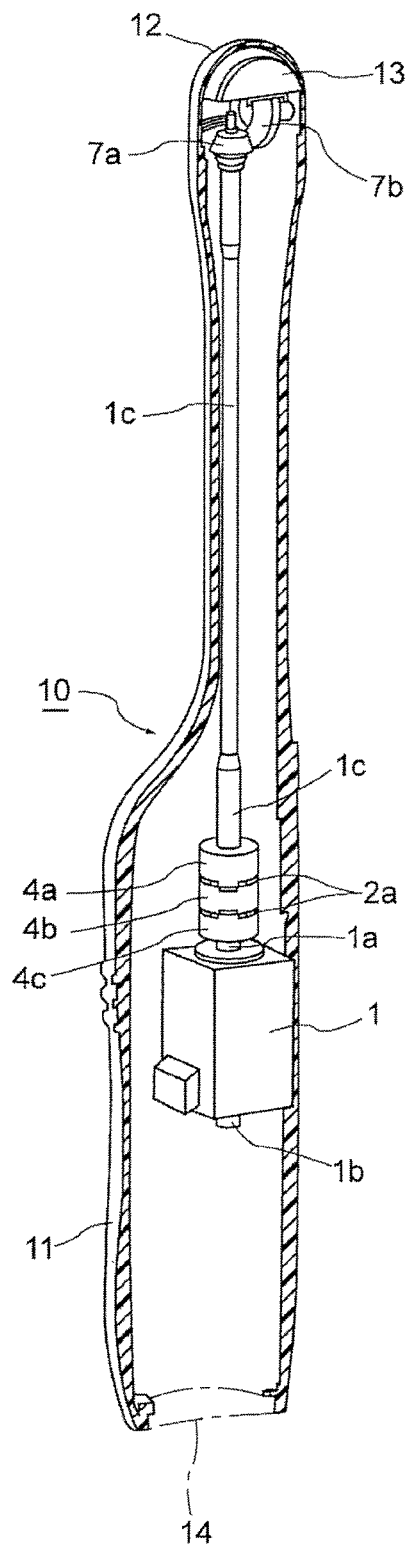
FIG. 7 is a longitudinal sectional drawing illustrating an overall configuration of a conventional mechanical scanning 3D ultrasonic transducer for medical ultrasonic diagnostic equipment.
Figure 8:
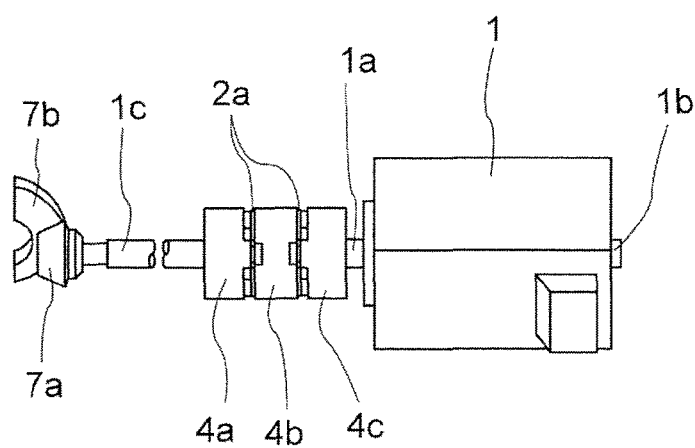
FIG. 8 is a side view of a coupling portion where a disk-type coupling is disposed between a driving motor and a bevel gear for swinging in a transducer main body of the ultrasonic transducer shown in FIG. 7.

Here, the ultrasonic transducer of the present invention has a configuration different from a configuration of the conventional ultrasonic transducer shown in FIG. 7 and FIG. 8 in that, as shown in FIG. 1, the ultrasonic transducer of the present invention employs a buffer for a coupling 2 and a flywheel 3 disposed on an output shaft 1b of the stepper motor 1 as the power source of the transducer, thus ensuring the reduced vibration and noise from the transducer.

Figure 3:
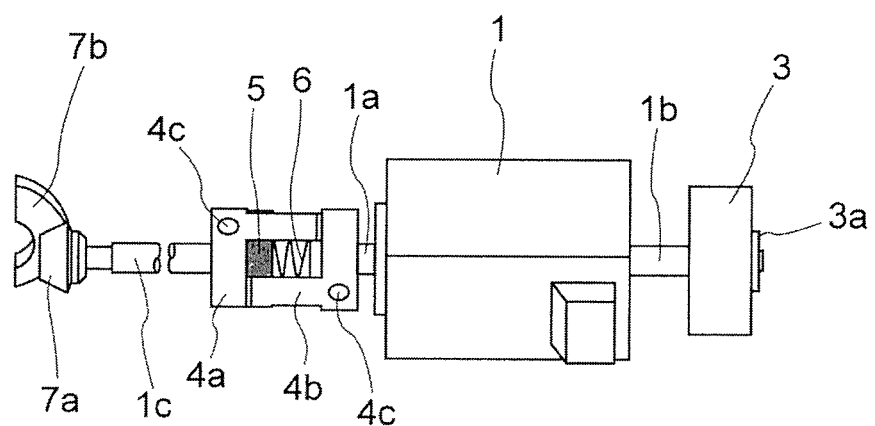
FIG. 3 is a side view of an embodiment including a coupling and a flywheel on a drive shaft of the driving motor. The coupling internally includes a buffer and a compression coil spring between a driving motor and bevel gears for swinging in a transducer main body of the ultrasonic transducer of the present invention shown in FIG. 1.
Figure 6:
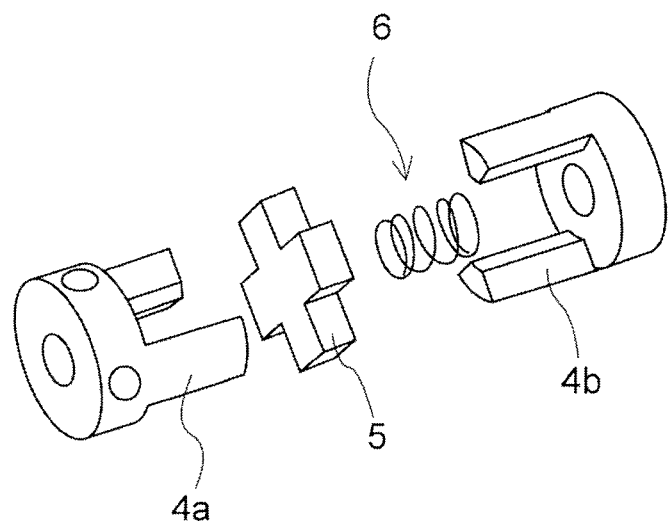
FIG. 6 is an exploded perspective view of the coupling internally including the buffer and the compression coil spring, which are shown in FIGS. 5(a)-5(b).

Namely, in Embodiment 1 of the ultrasonic transducer of the present invention, as shown in FIG. 3 and FIGS. 4(a)-4(b), the hub 4b is screwed by a screw 4c to one end portion of the output shaft 1a of the stepper motor 1 while the hub 4a is screwed by a screw 4c to the drive shaft 1c of the bevel gear 7a to be fixedly secured. Here, as shown in FIG. 4(a), the hubs 4a and 4b have end surfaces opposed to one another, and gaps g are disposed between the end surfaces to prevent both surfaces from contacting.

Then, as shown in FIG. 4(b), between cross-shaped arm portions of the hub 4b positioned between two pieces of the hubs 4a and 4b, a buffer 5, which is made of silicon rubber or the like and has a cross shape in plan view, is disposed. Both the hubs 4a and 4b are engaged to be coupled. This buffer 5 reduces the vibration transmission from the output shaft 1a of the stepper motor 1 to the transducer main body 13 via the coupling 2 and prevents generation of noise from the coupling 2. Here, the buffer 5 is required to have a hardness and a flexibility to the extent that the buffer 5 prevents the vibration and the noise, and surely transmits the torque of the output shaft 1a to the drive shaft 1c.

Figure 2:
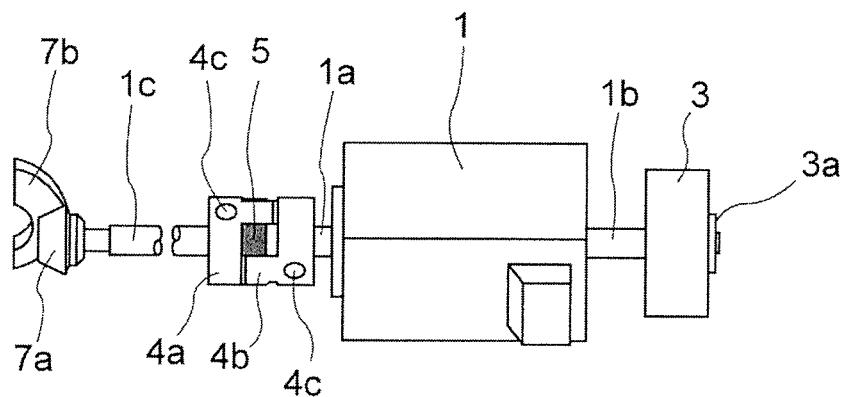
FIG. 2 is a side view of an embodiment including a coupling and a flywheel on a drive shaft of the driving motor. The coupling internally includes a buffer between a driving motor and bevel gears for swinging in a transducer main body of the ultrasonic transducer of the present invention shown in FIG. 1.

Furthermore, in this Embodiment 1, as shown in FIG. 2, the flywheel 3 is freely and loosely fitted to another end portion of the output shaft 1b of the stepper motor 1 via an oil layer, and is held by a washer 3a for prevention of dropping.

Thus, the flywheel 3 is swingably held (for example, the maximum reciprocation per second is six) on the other end portion of the output shaft 1b, thus ensuring the reduced vibration from the stepper motor 1 by the flywheel 3. If there is a space where the flywheel 3 is disposed, the flywheel 3 may be freely disposed at the one end portion of the output shaft 1b.

In Embodiment 2 of the ultrasonic transducer of the present invention, in addition to the buffer 5 and the flywheel 3 described in the above-described Embodiment 1, as shown in FIG. 3 and FIGS. 5(a)-(b), between the cross-shaped arm portions of the hub 4b positioned between the two pieces of the hubs 4a and 4b, a compression coil spring 6 is disposed along with the buffer 5, which is made of silicon rubber and or like and has a cross shape in plan view, such that the hub 4a screwed to the drive shaft 1c is pressed and biased from its back surface (see FIGS. 5(a)-(b)).

Thus, the compression coil spring 6 axially presses and biases the hub 4a screwed to the drive shaft 1c from its back surface. This causes the drive shaft 1c, where the small bevel gear 7a is fixedly secured at its tip, to act such that a gap (a backlash) between tooth surfaces of the small bevel gear 7a and the large bevel gear 7b. This configuration reduces variation of the engagement between both the bevel gears. This ensures the engagement accuracy during the normal and reverse swings so as to reduce the generation of the vibration and the noise.

The invention claimed is:
1. An ultrasonic device, comprising:
  a transducer main body;
  a power source, having an output shaft;
  a coupling, swingably and loosely fitted between the transducer main body and the output shaft of the power source that swings the transducer main body; and
  a flywheel, swingably and loosely fitted to the output shaft of the power source via an oil layer, and is held by a washer, wherein the coupling comprises:
- a first hub, disposed at a side of the transducer main body;
- a second hub, disposed at a side of the power source, and the first hub and the second hub are disposed opposed to one another;
- a buffer, disposed between the first hub and the second hub, wherein the buffer is configured to reduce generation of vibration and noise from the transducer main body; and
- a compression coil spring, disposed between the buffer and the second hub, wherein the compression coil spring axially biases the first hub and the second hub.

2. The ultrasonic device according to claim 1, wherein the coupling is disposed at one end portion of the output shaft, and
the flywheel is disposed at another end portion of the output shaft.

3. The ultrasonic device according to claim 1, wherein the buffer is made of silicon rubber.

4. The ultrasonic device according to claim 1, wherein the buffer has a cross shape in plan view.

5. The ultrasonic device according to claim 1, wherein the first hub has a first end surface, and
the second hub has a second end surface,
a gap is disposed between the first end surface and the second end surface.

* * * * *